(12) United States Patent
Lundstedt et al.

(10) Patent No.: US 8,410,174 B2
(45) Date of Patent: *Apr. 2, 2013

(54) METHOD FOR TREATING ARTHRITIS

(75) Inventors: Torbjörn Lundstedt, Uppsala (SE); Anna Skottner, Ekerö (SE); Elisabeth Seifert, Uppsala (SE)

(73) Assignee: AnaMar AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/426,096

(22) Filed: Mar. 21, 2012

(65) Prior Publication Data

US 2012/0178820 A1 Jul. 12, 2012

Related U.S. Application Data

(63) Continuation of application No. 11/639,190, filed on Dec. 15, 2006, now Pat. No. 8,148,429, which is a continuation of application No. 10/343,325, filed as application No. PCT/GB01/03534 on Aug. 7, 2001, now abandoned.

(30) Foreign Application Priority Data

Aug. 7, 2000 (GB) .................................. 0019357.3

(51) Int. Cl.
- A61K 31/155 (2006.01)
- A01N 37/52 (2006.01)
- A01N 37/30 (2006.01)

(52) U.S. Cl. .......................... 514/634; 514/632; 514/554

(58) Field of Classification Search .................. 514/554, 514/632, 634

See application file for complete search history.

(56) References Cited

U.S. PATENT DOCUMENTS

| | | | |
|---|---|---|---|
| 2,584,784 A | 2/1952 | Biswell | |
| 3,541,218 A | 11/1970 | Marshall et al. | |
| 3,591,636 A | 7/1971 | Houlihan et al. | |
| 3,592,852 A | 7/1971 | Houlihan et al. | |
| 3,592,935 A | 7/1971 | Houlihan et al. | |
| 3,816,530 A | 6/1974 | Linn | |
| 3,896,232 A | 7/1975 | Houlihan et al. | |
| 3,941,825 A | 3/1976 | Tomcufcik | |
| 3,975,533 A | 8/1976 | Kodama et al. | |
| 3,982,020 A | 9/1976 | Houlihan et al. | |
| 4,006,249 A | 2/1977 | Porter et al. | |
| 4,006,250 A | 2/1977 | Childress | |
| 4,060,640 A | 11/1977 | Kodama et al. | |
| 4,109,008 A | 8/1978 | Cognacq et al. | |
| 4,139,555 A | 2/1979 | Zerbes | |
| 4,312,886 A | 1/1982 | Gluckman | |
| 5,559,135 A | 9/1996 | Ashton et al. | |
| 5,599,984 A | 2/1997 | Bianchi et al. | |
| 5,750,545 A | 5/1998 | Akahoshi et al. | |
| 5,750,573 A | 5/1998 | Bianchi et al. | |
| 5,854,289 A | 12/1998 | Bianchi et al. | |
| 5,958,933 A | 9/1999 | Naftchi | |
| 6,413,962 B1 | 7/2002 | Naftchi | |
| 6,534,546 B1 | 3/2003 | Honda et al. | |
| 7,153,881 B2 | 12/2006 | Lundstedt et al. | |
| 8,148,429 B2* | 4/2012 | Lundstedt et al. | 514/634 |
| 2003/0091611 A1 | 5/2003 | Zahradka | |
| 2004/0019094 A1 | 1/2004 | Lundstedt et al. | |

FOREIGN PATENT DOCUMENTS

| | | |
|---|---|---|
| AU | 1339770 | 10/1971 |
| CA | 1079195 | 6/1980 |
| DE | 1165013 B | 3/1964 |
| DE | 1802394 | 5/1969 |
| DE | 2015321 A1 | 10/1970 |
| DE | 2020230 A | 12/1970 |
| DE | 3428342 A | 2/1986 |
| EP | 0165696 A2 | 12/1985 |
| EP | 0316852 A2 | 5/1989 |

(Continued)

OTHER PUBLICATIONS

Sikurova, L., et al., Chemical Abstract (CA) 133:359033, "Resorcylidene aminoguanidine improves the pathologically reduced fluidity of erythrocyte membranes in diabetes mellitus", Pharmazie, 55(9), 700-701, 2000.

Bruce, W. F., et al., Chemical Abstract (CA) 71:60991, "(Benzylideneamino) guanidines", German Patent No. DE 1802394, May 8, 1969.

Nishimura, T., et al., Chemical Abstract (CA) 88:131396, "Antiviral compounds. VIII. Synthesis and . . . of amidinohydrazones of alkoxybenzaldehydes . . . ", Kitasato Arch. Exp. Med., 48(4), 165, 1975.

(Continued)

*Primary Examiner* — Blessing Fubara
(74) *Attorney, Agent, or Firm* — Bacon & Thomas, PLLC

(57) ABSTRACT

The present invention relates to the use of compounds of general formula (I) as ligands to the melanocortin receptors and/or for treatment of disorders in the melanocortin system: wherein X is H or OH; R1, R2, R3, R4 and R5 are the same or different and are selected from hydrogen, halogen, alkyl having 1 to 5 carbon atoms, electron donor groups such as alkoxy having 1-5 carbon atoms or hydroxy, electron acceptor groups selected from cyano, nitro, trifluoroalkyl or amide; alkylamino, benzoyloxy, nitroxy, phenyl or sulpho; and the pharmacologically active salts thereof.

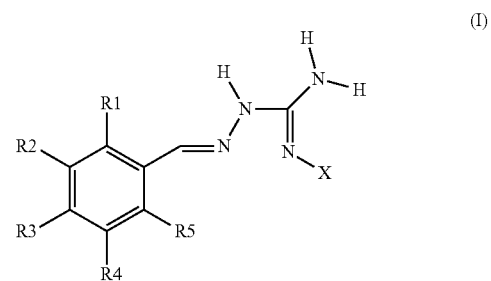

(I)

8 Claims, No Drawings

FOREIGN PATENT DOCUMENTS

| | | |
|---|---|---|
| EP | 0505322 A1 | 9/1992 |
| GB | 892117 | 3/1926 |
| GB | 0923398 | 4/1963 |
| GB | 1019120 A | 2/1966 |
| GB | 1204631 A | 9/1970 |
| GB | 1223491 | 2/1971 |
| GB | 1223492 A | 2/1971 |
| GB | 1223493 A | 2/1971 |
| GB | 1230468 A | 5/1971 |
| GB | 1368644 | 12/1971 |
| GB | 1381178 A | 1/1975 |
| GB | 1521594 A | 8/1978 |
| GB | 1527708 A | 10/1978 |
| IE | 44387 | 11/1981 |
| JP | 055062017 | 5/1980 |
| NZ | 529312 | 11/2003 |
| WO | 9214453 | 3/1992 |
| WO | 9303714 A | 4/1993 |
| WO | 96/30329 A1 | 10/1996 |
| WO | 9823267 A | 4/1998 |
| WO | 99/21571 A1 | 5/1999 |
| WO | 99/52936 A2 | 10/1999 |
| WO | 99/55679 A1 | 11/1999 |
| WO | 9964002 | 12/1999 |
| WO | 0009115 | 2/2000 |
| WO | 0035952 | 6/2000 |
| WO | 00/74742 A1 | 12/2000 |
| WO | 01/05401 A1 | 1/2001 |
| WO | 01/13921 A1 | 3/2001 |
| WO | 0125192 A | 12/2001 |
| WO | 02/11715 A2 | 2/2002 |
| WO | 02/12178 A1 | 2/2002 |
| WO | 02/080896 A1 | 10/2002 |

OTHER PUBLICATIONS

Miyamoto, Y., et al, Chemical Abstract (CA) 114:143359, "Synthesis of nitrogen-containing heterocycles. 5. A . . . 5-amino [1,2,4] triazolo [1,5-a] [1,3,5] triazine derivative", J. Heterocycl. Chem., 27(6), 1553-1557, 1990.

Holzer, W., et al., Chemical Abstract (CA) 118:254820, "The structure of guanylhydrazones derived from aromatic aldehydes", Monatsh. Chem., 123(12), 1163-1173, 1992.

Gyoergydeak, Z., et al., Chemical Abstract (CA) 124:8700, "1, 4, -Diacyl-3-acylamino-5-aryl-4, 5-dihydro-1H-1, 2, 4- . . . closure products of aromatic carbaldehyde (diaminorne . . . with acylating agents", Monatsh. Chem. 126(6/7), 733-746, 1995.

Houlihan, W. J., et al, Chemical Abstract (CA) 73:120368, "Hypotensive and antiinflammatory 1-(2,6-dimethylbenz . . . amino) guanidine", German Patent No. 2015321, Oct. 8, 1970.

Clement, B., et al., "Microsomal Catalyzed N-Hydroxylation of Guanabenz and Reduction of the N-Hydroxylated Metabolite: Characterization of the Two Reactions and Genotoxic Potential of Guanoxabenz", Chem. Res. Toxicol., 9 (4), 682-688, 1996.

Chang, Joseph, et al., "The antiinflammatory action of guanabenz is mediated through 5-lipoxygenase and cyclooxygenase inhibition", European Journal of Pharmacology, 142, 197-205, 1987.

Huszar, D., et al., "Targeted Disruption of the Melanocortin-4 Receptor Results in Obesity in Mice", Cell, 88, 131-41, Jan. 10, 1997.

Luger, T.A., et al, "Cutaneous Immunomodulation and Coordination of Skin Stress Responses by alpha-Melanocyte-Stimulating Hormone", Annal of the New York Academy of Sciences, 840, 381-394, 1998.

Ramachandra Rao, Y., "Isomeric Changes Involving Amidino & Thioamidino Systems: Part I-Conversion of 5-Amino / arlamino / alkylamino-2-arylamino-I,3,4-thiadiazoles into 5-Amino / arylamino / alkylamino-4-aryl-3-mercapto-I,2,4-triazotes", Dept. of Chemistry, Nagpur University, Nagpur / Dept. of Chemistry, Banaras Hindu University, Varanasi, 1967.

Knudtzon, J., "Alpha-Melanocyte Stimulating Hormone Increases Plasma Levels of Glucagon and Insulin in Rabbits", Life Sciences, 34, 547-554, Nov. 25, 1983.

Machado, R.D.P., et al., XP008089180, "Mechanisms of angiotensin-(1-7)-Induced inhibition of angiogenesis", Am. J. Physiol. Regulatory Integrative Comp. Physiol., 280, R994-R1000, 2001.

Phillips, P.G et al., XP008089179, "Nitric oxide modulates capillary formation at the endothelial cell-tumor cell interface", Am. J. Physiol. Lung Cell Mol, Physiol, 281, L278-L290, 2001.

Prusis, P., et al., XP008089162, "Synthesis and Quantitative Structure—Activity Relationship of Hydrazones of N-Amino-N'-hydroxyguanidine as Electron Acceptors for Xanthine Oxidase", J. Med. Chem., XP008089162, 47, 3105-3110, 2004.

Wikberg, J.E.S., "Melacortin receptors: perspectives for novel drugs", Eur. J. Pharmacol., 375, 295-310, 1999.

Strand, F. L., "New Vistas for Melanocortins: Finally, an Explanation for Their Pleiotropic Functions", Annals of the New York Academy of Sciences, 897, 1-16, 1999.

Tai, A. W., et al., "Novel N-Hydroxyguanidine Derivatives as Anticancer and Antiviral Agents", J. Med. Chem., 27, 236-238, 1984.

T'ang, A., et al., "Optimization of the Schiff Bases of N-Hydroxy-N'-aminoguanidine as Anticancer and Antiviral Agents", J. Med. Chem., 28,1103-1106, 1985.

Van Der Kraan, M., et al., "Expression of melanocortin receptors and pro-opiomelanocortin in the rat spinal cord in relation to neurotrophic effects of melanocortins", Molecular Brain Research, 63, 276-286, 1999.

Vergoni, A. V., et al., "Differential influence of a selective melanocortin MC4 receptor antagonist (HS014) on melanocortin-induced behavioral effects in rats", Eur. J. Pharmacol., 362, 95-101, 1998.

Versteeg, D. H. G., et al., "Meianocortins and cardiovascular regulation", Eur. J. Pharmacol., 360,1-14, 1998.

Wessells, H., et al., "Synthetic Melanotropic Peptide Initiates Erections in Men with Psychogenic Erectile Dysfunction: Double-blind, Placebo Controlled Crossover Study", J. Urol., 160, 389-393, 1998.

Cavallini, G., et al "Antibacterial Agents. Some New Guanylhydrazone Derivatives", J. Med. Pharm, Chem., 4(1), 177-182, 1961.

International Preliminary Examination Report issued on Nov. 29, 2002, in corresponding PCT Application No. PCT/GB01/03534 filed Aug. 7, 2001.

Official Action (Restriction Requirement), issued on Aug. 30, 2005, in parent U.S. Appl. No. 10/343,325, filed Jun. 23, 2003.

Official Action (Non-Final), issued on Feb. 8, 2006, in parent U.S. Appl. No. 10/343,325, filed Jun. 23, 2003.

Official Action (Notice of Non-Compliant Amendment & Interview Summary), issued on Jun. 22, 2006, in corresponding parent U.S. Appl. No. 10/343,325, filed Jun. 23, 2003.

Official Action (Final), issued on Dec. 15, 2006, in parent U.S. Appl. No. 10/343,325, filed Jun. 23, 2003.

Official Action (Non-Final), issued on Aug. 7, 2007, in parent U.S. Appl. No. 10/343,325, filed Jun. 23, 2003.

Official Action (Restriction Requirement) issued on Jun. 7, 2010, in related U.S. Appl. No. 11/798,669, filed May 16, 2007.

Official Action (Non-Final) issued on Dec. 8, 2010, in related U.S. Appl. No. 11/798,669, filed May 16, 2007.

Dambrova M.; Ph.D. Thesis, "Discovery of N-hydroxyguanidines as Novel Electron Acceptors of Xanthine Oxidase: Potential new drugs for treatment of ischemia and repertusion injury", University of Uppsala, Oct. 29, 1999.

Uhlen, S,, et al., "Characterization of Enzymatic Activity for Biphasic Competition by Guanoxabenz (1-(2,6-dichlorobenzylidene-amino)-3-hydroxyguanidine) at alpha-2-Adrenoceptors: I. Description of an enzymatic activity in spleen membranes", Biochemical Pharmacology, 56, 1111-1119, 1998.

Dambrova, M., et al "Characterization of Guanoxabenz Reducing Activity in Rat Brain", Pharmacology & Toxicology, 83, 158-163, 1998.

Dambrova, M., et al., "Characterization of the Enzymatic Activity for Biphasic Competition by Guanoxabenz (1-(2,6-dichlorobenzylidene-amino)-3-hydroxyguanidine) at alpha-2-Adrenoceptors: II. Description of a Xanthine-Dependent Enzymatic Activity in Spleen Cytosol", Biochemical Pharmacology, 56, 1121-1128, 1998.

Dambrova, M., et al "Identification of a N-hyxdroxyguanidine reducing activity of xanthine oxidase", Eur. J. Biochem., 257, 178-184, 1998.

Dambrova, M., et al., "Synthesis and Evaluation of Hydrazones of N-Amino-N'-Hydroxyguanidine as Novel Alternative Electron Acceptors for Xanthine Oxidase", Manuscript—Medicinal Chemistry of N-hydroxyguanidine derivatives, University of Uppsala, 1-10, Figs 1-6, Oct. 29, 1999.

Dambrova, M., et al., "PR5—A Member of a Novel Class of Xanthine Oxidase Electron-Acceptors, Inhibits the Generation of Free Radicals", Manuscript—Xanthine Oxidase Electron Acceptors-Inhibitors, University of Uppsala, 1-12, Oct. 29, 1999.

Veveris, M., et al., "Cardioprotective effects of N-hydroxyguanidine PR5 in myocardial ischaemia and reperfusion in rats", British Journal of Pharmacology, 128(5), 1089-1097, 1999.

Sotolongo, Jr., et al. "Effects of Guanabenz on Bladder Function After Spinal Cord Injury," Neurourology and Urodynamics (1989), 8: 245-254.

Kazic, T. et al., "Central presynaptic alpha2 agonists guanabenz and clonidine act as aplha1 adrenoceptor antagonists in the isolated vas deferens of the guinea pig," IUGOSL. Physiol. Pharmacol. ACTA (1994), 30 (1), 25-34, XP001098531.

Osawa Y, et al., "Inactivation of penile nitric oxide synthase by Guanabenz, and antihypertensive agent: Potential implications in drug induced impotence," FASEB Journal, vol. 9, No. 6, 1995, p. A1495, XP001095624.

Nakatsuka, Mikiya, et al. "Metabolism-based inactivation of penile nitric oxide synthase activity by Guanabenz," Drug Metabolism and Disposition, vol. 26, No. 5, May 1998, pp. 497-501, XP001095628.

Benelli A., et al., "Male sexual behavior: further studies on the role of apha 2-adrenoceptors," Pharmacological Research: The Official Journal of the Italian Pharmacological Society, England, Jul.-Aug. 1993, vol. 28, No. 1, Jul. 1993, pp. 35-45, XP001095156.

William O. Foye et al., "Synthesis and Biological Activity of Guanylhydrazones of 2- and 4-Pyridine and 4-Quinoline Carboxaldehydes," Journal of the American Pharmaceutical Association, vol. 79, No. 6, Jun. 1990, pp. 527-530, XP002180467.

Dimmock J.R., et al., "Evaluation of the Thiosemicarbazones of Some Aryl Alkyl Ketones and Related Compounds for Anticonvulsant Activities," European Journal of Medicinal Chemistry, Editions Scientifique Elsevier, Paris, FR, vol. 26, No. 5, 1991, pp. 529-234, XP002014742.

Southan Garry J., et al., "Hydroxyguanidines inhibit peroxynitrite-induced oxidation," Free Radical Biology & Medicine, vol. 25, No. 8, Nov. 15, 1998, pp. 914-925, XP002209697.

Dambrova et al, ("N-hydroxyguanidine Compound 1-(3, 4-dimethoxy-2-chlorobenzylideneamino)-3-hydroxyguanidine inhibits the Xanthine Oxidase Mediated Generation of Superoxide Radical" in Archives of Biochemistry and Biophysics), May 1, 2000.

* cited by examiner

METHOD FOR TREATING ARTHRITIS

This application is a continuation application of U.S. patent application Ser. No. 11/639,190, filed Dec. 15, 2006, which has issued as U.S. Pat. No. 8,148,429 on Apr. 3, 2012, which is a continuation of Ser. No. 10/343,325, filed Jun. 23, 2003, which is a PCT National Stage Application of PCT/GB2001/003534 filed Aug. 7, 2001 (of which the entire disclosure of the pending, prior application is hereby incorporated by reference).

The present invention relates to the use of benzylideneaminoguanidines and hydroxyguanidines for the treatment of obesity, anorexia, inflammation, mental disorders and other diseases associated with the melanocortin receptors or related systems, e.g. the melanocyte stimulating hormones.

A number of large linear and cyclic peptides are known in the art which show high specific binding to melanocortin (MC) receptors. The agonistic and/or antagonistic properties of these peptides are also known. See for example "Melanocortin Receptor ligands and methods of using same" by Dooley, Gillen and Houghten (WO99/21571). There remains, however, a need to provide low molecular weight compounds showing agonistic or antagonistic properties to the melanocortin receptors.

Previously known in the art are hydroxyguanidines (e.g. WO98/23267), which have proven activity against xanthine oxidase/xanthine dehydrogenase enzymes. Other compounds known in the art are benzylideneamino guanidines which have shown anti-depressive effects (U.S. Pat. No. 4,060,640). Other examples of pharmacologically active guanidines known in the art are described in U.S. Pat. No. 3,982,020 and GB 1223491. Other application areas are also known in the art and are described in U.S. Pat. No. 3,896,332, DE 1165013, and U.S. Pat. No. 3,941,825. Guanabenz is compound which is well known in the art as an antihypertensive drug (US Pharmacopeia, 1999, The United States Pharmacopeial Convention, Inc, ISBN 1-889788-03-1). Whilst Guanabenz might appear to be structurally similar to the compounds in the present invention, it shows no affinity to the melanocortin receptors. Therefore it is very surprising that the benzylideneamino guanidine compounds in the present invention show affinity to the melanocortin receptors as agonist and/or antagonists.

One aspect of the present invention is therefore to provide low molecular weight compounds showing activity on melanocortin receptors and which may be taken up after per oral administration and which may penetrate well through the blood brain barrier.

The present invention provides the use of compounds of the general formula (I) as ligands to the melanocortin receptors and/or for treatment of disorders in the melanocortin system:

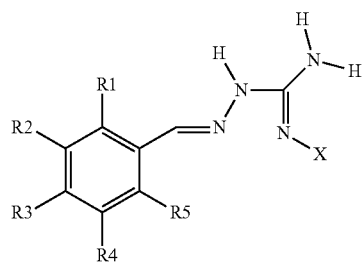

wherein X is H or OH;
$R_1, R_2, R_3, R_4$ and $R_5$ are the same or different and are selected from hydrogen, halogen, alkyl having 1 to 5 carbon atoms, electron donor groups such as alkoxy having 1-5 carbon atoms or hydroxy, electron acceptor groups selected from cyano, nitro, trifluoroalkyl or amide; alkylamino, benzoyloxy, nitroxy, phenyl or sulpho; and the pharmacologically active salts thereof.

When used in the foregoing definitions, the term alkyl is meant to include straight or branched chain hydrocarbon groups as well as alicyclic groups; the term alkoxy is meant to include straight or branched chain alkoxy groups or heterocyclic groups; and the term halogen includes fluoro, chloro, bromo and iodo.

Preferably, the "alkyl having 1 to 5 carbon atoms" is a lower alkyl such as Methyl, ethyl, propyl or iso-propyl.

Preferably, the "alkoxy having 1 to 5 carbon atoms" is a lower alkoxy such as methoxy, ethoxy, propoxy or iso-propoxy.

Preferably, the halogen is fluoro or chloro.

Preferably, the trifluoroalkyl is trifluoromethyl, trifluoroethyl, trifluoropropyl or trifluoroisopropyl.

The term "alkylamino" refers preferably to groups having 2-6 carbon atoms, particularly dialkylamino groups, and most preferably dimethylamino or diethylamino.

Two or more of $R_1$-$R_5$ may be linked by a linker group such as —O—(CH$_2$)$_n$—O—, where n is preferably 1, 2 or 3. Most preferably the linker is a methylenedioxy group, particularly preferably a 2,3- 3,4- or 4,5-methylenedioxy group.

Further preferred compounds are those wherein $R_1$ is nitroxy or sulpho; $R_3$ is phenyl; and $R_1$, $R_2$ and $R_3$ are all benzoyloxy.

Particularly preferred compounds are those wherein 1 or 2 of $R_1$, $R_2$, $R_3$, $R_4$ and $R_5$ are H.

The compounds of formula (I) have basic properties and, consequently, they may be converted to their therapeutically active acid addition salts by treatment with appropriate physiologically acceptable acids, e.g. inorganic acids such as hydrochloric, hydrobromic, hydroiodic, sulphuric, nitric and phosphoric acid, or organic acids such as acetic, propanoic, glycolic, lactic, malonic, succinic, fumaric, tartaric, citric, pamoic or para-toluene-sulphonic acid.

Conversely, the salt form may be converted into the free base form by treatment with alkali.

The present invention relates the use of benzylideneaminoguanidines and hydroxyguanidines. Some of the compounds of the present invention have been biologically tested in the melanocortin system and have surprisingly been shown to be capable of binding to melanocortin receptors as well as showing activity in functional assays.

Some of the compounds of the present invention are either agonists or antagonists of a specific MC-receptor or of a number of MC-receptors, e.g. MC1, MC3, MC4 or/and MC5 receptors.

The MC-receptors belong to the class of G-protein coupled receptors which are all built from a single polypeptide forming 7 transmembrane domains. Five such receptors types, termed MC1, MC2, MC3, MC4 and MC5, have been described. The MC receptor's signaling is mainly mediated via cAMP but also other signal transduction pathways are known. They are distinctly distributed in the body.

MC-receptors are linked to a variety of physiological actions that are thought to be mediated by distinct subtypes of the MC-receptors. In many cases, however, it is not entirely clear which of the subtypes is responsible for the effect.

It has long been known that MSH-peptides may affect many different processes such as motivation, learning, memory, behaviour (including feeding and sexual), inflammation (including immunostimulatory and immunosuppressive), body temperature, pain perception, blood pressure, heart rate, vascular tone, brain blood flow, trophic effects in different organs, nerve growth, placental development, endocrine and exocrine functions, aldosterone synthesis and release, thyroxin release, spermatogenesis, ovarian weight, prolactin and FSH secretion, effects on other hormones, uterine bleeding in women, sebum and pheromone secretion, blood glucose levels, intrauterine foetal growth, as well as other events surrounding parturition and natriuresis (Eberle, A N: The melanotropins: Chemistry, physiology and mechanisms of action. Basel: Karger, Switzerland. 1988, ISBN 3-8055-4678-5; Gruber, and Callahan, Am. J. Physiol. 1989, 257, R681-R694; De Wildt et al., J. Cardiovascular Pharmacology. 1995, 25, 898-905), as well as inducing natriuresis (Lin et al., Hypertension. 1987, 10, 619-627).

It is also well-known that the immunomodulatory action of α-MSH includes both immunostimulatory and immunosuppressive effects. Several studies have shown that α-MSH antagonizes the effects of pro-inflammatory cytokines such as IL-1α, IL-1β, IL-6 and TNFα, and induces the production of the anti-inflammatory cytokine, IL-10 (for review see Catania & Lipton, 1993).

Eating behaviour is regulated by a complex network of physiological regulatory pathways that involve both the central nervous system and peripheral sites. Factors such as leptin, insulin, NPV (neuropeptide Y), orexins, CRF (Corticotropin-Releasing Factor, release hormone) and melanocortic peptides (Schwartz; Nature Medicine 1998, 4, 385-386) are known to control the amount of food intake both during short and long term, which may affect body weight, body fat mass and growth rate. Recent studies have shown a role of MC-receptors, especially the MC4 receptor, for control of food intake, and there is evidence indicating that the melanocortins and the MC4 receptor are important factors downstream of leptin. Intracerebroventricular injections of the melanocortic peptides α-MSH and ACTH(1-24) have been shown to markedly inhibit feeding (Poggioli et al., Peptides, 1986, 7, 843-848; Vergoni et al., Neuropeptides, 1986, 7, 153-158).

The MC5-receptor has recently been attributed a role in control of exocrine gland function (van der Kraan, et al., Endocrinol. 1998, 139, 2348-2355; Chen et al., Cell. 1997, 91, 789-798).

In addition, the melanocortic peptides have distinct effects on sexual functions in that they cause erection in males (Donovan, Psychol. Med. 1978, 8, 305-316), presumably mediated by a central agonistic effect of the peptide on MC-receptors. It has also been shown that a MC-receptor blocker could inhibit the erectogenic effect of melanocortic peptides (Vergoni et al., Eur. J. Pharmacol, 1998, 362; 95-101).

Compounds of formula (I) and/or their pharmaceutically acceptable salts have valuable pharmacological properties, making them useful for the treatment of mental disorders such as psychoses, depression, anxiety, senile dementia, Alzheimer's disease, drug abuse disorders and eating disorders such as anorexia and bulimia.

Compounds of formula (I) and/or their pharmaceutically acceptable salts have valuable pharmacological properties, making them useful for the treatment of dysfunctions of the endocrine system and other hormonal systems such as excessive menstruations, endometriosis, events related to parturition, dysfunctions related to prolactin, dysfunctions related to growth hormone, dysfunctions related to testosterone, dysfunctions related to estrogen, dysfunctions related to glucocorticoids, dysfunctions related to luteinizing hormone and follicle stimulating hormone, inducing abortion, for prevention of abortion and/or for treatment of events related to parturition.

Compounds of formula (I) and/or their pharmaceutically acceptable salts have valuable pharmacological properties, making them useful for the treatment of sexual functions/dysfunctions such as inducing erection in man, to induce erection in animal breeding, to stimulate intercourse in animals which are difficult to mate, in particular rare species or valuable stains, pets, cats, dogs, horses or to reduce sexual behaviour in animals, e.g. for pets, cats etc., to treat impotence and disorders related to sexual drive, including lack of sexual drive or abnormal sexual drive in both men and women.

Compounds of formula (I) and/or their pharmaceutically acceptable salts have valuable pharmacological properties, making them useful for the treatment of inflammation such as inflammations related to the production of nitric oxide, inflammation related to increased amounts (upregulated amounts) of inducible nitric oxide synthase, inflammation related to activation of transcriptional activators, inflammation related to nuclear factor kappa beta, inflammation related to macrophages, neutrophils, monocytes, keratinocytes, fibroblasts, melanocytes, pigment cells and endothelial cells, inflammation related to increased production and/or release of inflammatory cytokines, such as e.g. interleukins, in particular interleukin 1 (IL-1), interleukin 6 (IL-6) and tumor necrosis factor α (TNF-α).

In the present specification, "increased production" refers to increased formation, increased release, or increased amount of an endogenous compound locally, regionally or systemically in a patient compared to the amount of said endogenous compound in a healthy individual. In the present specification, "upregulated" refers to an increased activity or amount of the compound compared with that in a healthy individual.

In the present specification, "decreased production" refers to decreased formation, decreased release, or decreased amount of an endogenous compound in a patient compared to the amount of said endogenous compound in a healthy individual. In the present specification, "downregalated" refers to a decreased activity or amount of the compound compared with that in a healthy individual.

In particular, positive treatment effects or preventive effects may be seen in conditions where inflammation or an inflammatory-like condition is caused by or being associated with one or more of the following: allergy, hypersensitivity, bacterial infection, viral infection, inflammation caused by toxic agent, fever, autoimmune disease, radiation damage by any source including UV-radiation, X-ray radiation, γ-radiation, α- or β-particles, sun burns, elevated temperature or mechanical injury. Moreover, inflammation due to hypoxia, which is optionally followed by reoxygenation of the hypoxic area, is typically followed by severe inflammation, which condition may be positively affected by treatment with a compound of the invention.

In very specific embodiments of the invention, a compound of the invention may be administered for the prevention or therapeutic treatment of inflammatory diseases of the skin (including the dermis and epidermis) of any origin, including skin diseases having an inflammatory component. Specific examples of this embodiment of the invention include treatment of contact dermatitis of the skin, sunburns of the skin, burns of any cause, and inflammation of the skin caused by chemical agents, psoriasis, vasculitis, pyoderma gangrenosum, discoid lupus erythematosus, eczema, pustulosis palmoplantaris, and phemphigus vulgaris.

Also comprised by the invention is the administration of a compound of formula (I) or a pharmacologically acceptable salt thereof for the treatment of an inflammatory disease in the abdomen, including an abdominal disease having an inflammatory component. Specific examples of the treatment of such a disease with a compound of the invention are gastritis, including one of unknown origin, gastritis perniciosa (atrophic gastritis), ulcerous colitis (colitis ulcerosa), morbus Crohn, systemic sclerosis, ulcus duodeni, coeliac disease, oesophagitis and ulcus ventriculi.

Comprised by the invention is also the administration of a compound of formula (I) or a pharmacologically acceptable salt thereof for the treatment of systemic or general and/or local immunological diseases, including those of an autoimmune nature, and other inflammatory diseases of a general nature. Specific examples include treatment of rheumatoid arthritis, psoriatic arthritis, systemic sclerosis, polymyalgia rheumatica, Wegener's granulomatosis, sarcoidosis, eosinophilic fasceitis, reactive arthritis, Bechterew's disease, systemic lupus erythematosus, arteritis temporalis, Behcet's disease, morbus Burger, Good Pastures' syndrome, eosinophilic granuloma, fibromyalgia, myositis, and mixed connective tissue disease. Included therein is also arthritis, including arthritis of unknown origin.

Further included in the invention is administration of a compound of formula (I) or a pharmacologically acceptable salt thereof for the treatment of a disease of the peripheral and/or central nervous system related to inflammation. Included in this aspect of the invention is the treatment of cerebral vasculitis, multiple sclerosis, autoimmune ophthalmitis and polyneuropathia. Comprised by the invention is also the administration of a compound of the invention for the treatment of an inflammation of the central nervous system to prevent apoptotic cell death. Moreover, as some of the compounds of the invention show a distinct ability to induce nerve regeneration, positive treatment effects are often seen in central nervous system diseases involving damage of cells in this region. This aspect of the invention also includes treatment of traumatic injuries to the central nervous system, brain edema, multiple sclerosis, Alzheimer's disease, bacterial and viral infections in the central nervous system, stroke, and haemorrhagia in the central nervous system.

Comprised by the invention is also the administration of a compound of formula (I) or a pharmacologically acceptable salt thereof for the treatment of diseases of the eye and tear glands related to inflammation. Specific examples of such diseases comprise anterior and posterior uveitis, retinal vasculitis, optic neuritis, optic neuromyelitis, Wegener's granulomatosis, Sjögren's syndrome, episcleritis, scleritis, sarcoidosis affecting the eye and polychondritis affecting the eye.

Comprised by the invention is also the administration of a compound of formula (I) or a pharmacologically acceptable salt thereof for the treatment of diseases of the ear related to inflammation, specific examples of which include polychondritis affecting the ear and external otitis.

Comprised by the invention is also the administration of a compound of formula (I) or a pharmacologically acceptable salt thereof for the treatment of diseases of the nose related to inflammation, specific examples of which are sarcoidosis, polychondritis and mid-line granuloma of the nose.

Comprised by the invention is also the administration of a compound of formula (I) or a pharmacologically acceptable salt thereof for the treatment of diseases related to inflammation of the mouth, pharynx and salivary glands. Specific examples include Wegener's granulomatosis, mid-line granuloma, Sjögren's syndrome and polychondritis in these areas.

Included in the invention is also the administration of a compound of formula (I) or a pharmacologically acceptable salt thereof for the treatment of diseases related to inflammation in the lung. Specific examples include treatment of idiopathic alveolitis, primary pulmonary hypertension, bronchitis, chronic bronchitis, sarcoidosis, alveolitis in inflammatory systemic disease, pulmonary hypertension in inflammatory systemic disease, Wegener's granulomatosis and Good Pastures' syndrome.

Comprised by the invention is also the administration of a compound of formula (I) or a pharmacologically acceptable salt thereof for the treatment of diseases related to the inflammation of the heart. Specific examples include treatment of pericarditis, idiopathic pericarditis, myocarditis, Takayasus' arteritis, Kawasaki's disease, coronary artery vasculitis, pericarditis in inflammatory systemic disease, myocarditis in inflammatory systemic disease, endocarditis and endocarditis in inflammatory systemic disease.

Comprised by the invention is also the administration of a compound of formula (I) or a pharmacologically acceptable salt thereof for the treatment of diseases related to inflammation of the liver. Specific examples include treatment of hepatitis, chronic active hepatitis, biliary cirrhosis, hepatic damage by toxic agents, interferon induced hepatitis, hepatitis induced by viral infection, liver damage induced by anoxia and liver damage caused by mechanical trauma.

Comprised by the invention is also the administration of a compound of formula (I) or a pharmacologically acceptable salt thereof for the treatment of diseases related to inflammation of the pancreas. Specific examples include treatment (and prevention) of diabetes mellitus, acute pancreatitis and chronic pancreatitis.

Comprised by the invention is also the administration of a compound of formula (I) or a pharmacologically acceptable salt thereof for the treatment of diseases related to the inflammation of the thyroidea. Specific examples of these embodiments of the invention include treatment of thyreoiditis, autoimmune thyreoiditis and Hashimoto's thyreoiditis.

Comprised by the invention is also the administration of a compound of formula (I) or a pharmacologically acceptable salt thereof for the treatment of diseases related to inflammation of the kidney. Specific examples include treatment of glomerulonephritis, glomerulonephritis in systemic lupus erythematosus, periarteritis nodosa, Wegener's granulomatosis, Good-Pastures' syndrome, HLAb27 associated diseases, IgA nephritis (IgA=Immunoglobulin A), pyelonephritis, chronic pyelonephritis and interstitial nephritis.

Comprised by the invention is also the administration of a compound of formula (I) or a pharmacologically acceptable salt thereof for the treatment of diseases related to the inflammation of the joints. Specific examples include treatment of Bechterew's disease, psoriatic arthritis, rheumatoid arthritis, arthritis in colitis ulcerosa, arthritis in morbus Crohn, affection of joints in systemic lupus erythematosus, systemic sclerosis, mixed connective tissue disease, reactive arthritis, Reiter's syndrome. Moreover, included in this embodiment of the invention is treatment of arthrosis of any joint, in particular arthrosis of finger joints, the lone and the hip.

Comprised by the invention is also the administration of a compound of formula (I) or a pharmacologically acceptable salt thereof for the treatment of diseases related to the inflammation of blood vessels. Specific examples include treatment of arteritis temporalis, periarteritis nodosa, arteriosclerosis, Takayasus' arteritis and Kawasaki's disease. Particularly advantageous is the capacity of some compounds of the invention to afford protection against and prevention of arteriosclerosis. This is in part due to the capacity of some compounds of formula (I) or the pharmacologically acceptable salts thereof to prevent the induction of inducible nitric oxide synthesis (iNOS) caused by the action of oxidized Low Density Lipoprotein on endothelial cells and blood vessel walls.

Comprised by the invention is also the administration of a compound of the invention for the treatment of drug-induced disorders of the blood and lymphoid system, including the treatment of drug-induced hypersensitivity (including drug hypersensitivity) affecting blood cells and blood cell forming organs (e.g. bone marrow and lymphoid tissue). Specific embodiments of this aspect of the invention include the treatment of anemia, granulocytopenia, thrombocytopenia, leukopenia, aplastic anemia, autoimmune hemolytic anemia, autoimmune thrombocytopenia and autoimmune granulocytopenia.

The compounds of the invention may also be administered for the treatment of fast allergic disorders (Type I allergy). Included in this embodiment of the invention is the treatment of anaphylactic reactions, anaphylactoid reactions, asthma, asthma of allergic type, asthma of unknown origin, rhinitis, hay fever and pollen allergy.

Comprised by the invention is also the administration of a compound of formula (I) or a pharmacologically acceptable salt thereof for the treatment of inflammation related to infections of any origin. Specific examples include treatment of inflammation secondary to infection caused by virus, bacteria, helminths and protozoae.

Comprised by the invention is also the administration of a compound of formula (I) or a pharmacologically acceptable salt thereof for the treatment of inflammations related to trauma and/or tissue injury of any origin.

Compounds of formula (I) or pharmaceutically acceptable salts thereof have valuable pharmacological properties, making them useful for the treatment of disorders of the cardiovascular system such as disorders related to blood pressure, heart rate, vascular tone, natriuresis, bleeding, shock, disorders related to ischemia, infarction, repercussion injuries, arrhythmias of the heart, in particular during ischemia, or for the treatment of arrhythmias associated with reoxygenation of a previously ischemic period of the heart.

Compounds of formula (I) or the pharmaceutically acceptable salts thereof have valuable pharmacological properties, making them useful for the treatment of pain such as pain of central origin, pain seen after damage to the CNS, stroke, infarction, pain of peripheral origin, chronic pain, neuropathies and disorders where a treatment effect is achieved by stimulation of receptors in the periaqueductal grey area.

Because of the capacity of compounds of the invention to stimulate pigment formation in epidermal cells, compounds of the invention may be also useful for inducing skin tanning for cosmetic reasons, for treatment of vitiligo, or any other condition where darkening of skin color is desired. Moreover, because of the ability of compounds of the invention to inhibit pigment formation in cells of the skin, they may also be useful for inducing lighter skin color for cosmetic reasons, or during any condition where a lighter color of skin is desired.

Compounds of formula (I) or the pharmaceutically acceptable salts thereof have valuable pharmacological properties, making them useful to cause skin tanning, darkening the colour of the skin, to induce melanin synthesis in the skin, to reduce skin twining, lightening the colour of the skin, to reduce or block melanin synthesis in the skin, to cause anti-inflammatory actions in the skin, to modulate epidermal growth, to improve wound healing, to treat acne, seborrhoea, acne roseacea, conditions related to malfunctions of the glands of the skin, e.g. sebacous glands and over or under-production of sebum.

Compounds of the invention are useful for inhibiting or stimulating the in vivo formation of second messenger elements such as cAMP. Such inhibition/stimulation may be used in cells or crushed cell systems in vitro, e.g. for analytical or diagnostic purposes.

For analytical and diagnostic purposes the compounds of the invention may be used in radioactive form where they comprise one or more radioactive labels or gamma or positron emitting isotopes, to be used in radioligand binding for the quantification as well as tissue localisation of MC-receptors, for analysis of dissociation/association constants, and for imaging of in vivo binding by the use of scintigraphy, positron emission tomography (PET) or single photon emission computed tomography (SPECT), or for the diagnosis of disease and treatment of any malignancy where the malignant cells contain MC receptors.

Alternatively the compounds of the invention can be labelled with any other type of label that allows detection of the respective compound, e.g. fluorescence, biotin, NMR, MRI, or labels activated by gamma-irradiation, light photons or biochemical processes, or by light or UV-light (the latter in order to obtain a compound useful for covalent labelling of MC receptors by a photoaffinity technique).

Compounds of formula (I) or the pharmacologically acceptable salts thereof may also be tagged with a toxic agent (i.e. doxorubicin, ricin, diphtheria toxin or other) and used for targeted delivery to malignant cells bearing MC receptors, or tagged with a compound capable of activating the endogenous immune system for triggering the immune system (for example a compound, monoclonal antibody or other, capable of binding to a T-cell antigen, e.g. CD3 or other) for treatment of malignancies and other MC receptor expressing diseases. The thus formed hybrid compound will direct cytotoxic cells to the malignant melanoma cells or the MC1-receptor bearing malignant cells and inhibit the tumor growth.

Compounds of formula (I) or a pharmacologically acceptable salt thereof may be attached to the antibody chemically by covalent or non-covalent bond(s).

Compounds of the invention may be used for the treatment and diagnosis of diseases, disorders and/or pathological conditions in an animal, in particular in man.

The present invention also relates to a pro-drug which, upon administration to an animal or a human, is converted to a compound of the invention. Pro-drugs of the compounds of formula (I) and their pharmacologically acceptable salts may be used for the same purposes as described in this specification for the compounds of the invention, as well as is disclosed in the Examples given below.

The compounds of the present invention may be bound covalently or non-covalently to one or several of other molecule(s) of any desired structure(s); the thus formed modified compound or complex may be used for the same purposes as described in this specification for the compounds of the invention, as well as is disclosed in the Examples given below. In a particularly important embodiment of the invention, a radioactively-labeled molecule is covalently bound to a compound of formula (I) or a pharmacologically acceptable salt thereof so as to make a compound of formula (I) or a pharmacologically acceptable salt thereof radioactively labeled.

The invention also relates to uses of compounds of the invention for various medical and veterinary practices related to melanocyte stimulating hormone receptors.

Compounds of the invention have an effect on xanthine oxidase in mammals, including humans.

Methods of Preparation

The compounds having the general formula (I) may be prepared by the following general method.

Method 1.

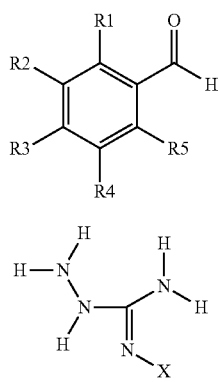

A compound of formula (II) wherein X, R1, R2, R3, R4 and R5 are as previously defined, is reacted with aminoguanidine (III) or a salt or protected form thereof wherein X is as previously defined, followed if necessary or desired by deprotection to yield a compound of formula (I).

EXAMPLES

The following examples are intended to illustrate but not to limit the scope of the invention, although the compounds named are of particular interest for the intended purposes. These compounds have been designated by a number code, a:b, where a means the number of example, wherein the preparation of the compound is described, and b refers to the order of the compound prepared according to that example. Thus example 1:2 means the second compound prepared according to Method 1 (see example 1).

Example 1

IR, NMR, MS and elementary analysis have confirmed the structures of the compounds. When melting points (m.p.) are given, these are uncorrected.
Preparation of Compound 1:1
A solution of 2-chloro-3,4-dimethoxybenzaldehyde (1.0 g, 5 mmol), aminoguanidine bicarbonate (0.68 g, 5 mmol) and acetic acid (1 ml), in 15 ml of methanol was heated at reflux for 10 min. The reaction mixture was cooled down to 0° C. and the residue was filtered off. The filtrate was evaporated under vacuum and the product was crystallised from ethanol Yield of the title compound 1:1 was 1.1 g (70%), M.p. 198-200° C.
Preparation of Compounds 1:2-1:164
Compounds 1:2-1:164 were prepared using essentially the same approach as for 1:1 by using Method 1. Compounds with their data was as follows:

1. N-(2-chloro-3,4-dimethoxybenzylideneamino)guanidine acetate, m.p. 198-200° C.
2. N-(3-Bromobenzylideneamino)-N'-hydroxyguanidine tosylate, m.p. 177-178.5° C.
3. N-(3-Bromo-4-methoxybenzylideneamino)-N'-hydroxyguanidine tosylate, m.p. 209-210.5° C.
4. N-(5-Chloro-2-nitrobenzylideneamino)-N'-hydroxyguanidine tosylate, m.p. 180-181° C.
5. N-(2,4-Dihydroxybenzylideneamino)-N'-hydroxyguanidine tosylate, m.p. 194-195° C.
6. N-(2,3-Dihydroxybenzylideneamino)-N'-hydroxyguanidine tosylate, m.p. 108-109° C.
7. N-(2,4,5-Trimethoxybenzylideneamino)-N'-hydroxyguanidine tosylate, m.p. 98.5-99.5° C.
8. N-(3-Nitrobenzylideneamino)-N'-hydroxyguanidine tosylate, m.p. 204.5-206° C.
9. N-(4,5-Methylenedioxy-2-nitrobenzylideneamino)-N'-hydroxyguanidine tosylate, m.p. 108-111° C.
10. N-(3,4,5-Trimethoxybenzylideneamino)-N'-hydroxyguanidine tosylate, m.p. 139-141° C.
11. N-(4-Chloro-3-nitrobenzylideneamino)-N'-hydroxyguanidine tosylate, m.p. 184-187° C.
12. N-(4-Methoxybenzylideneamino)-N'-hydroxyguanidine tosylate, m.p. 175-177° C.
13. N-(2-Bromobenzylideneamino)-N'-hydroxyguanidine tosylate, m.p. 148.5-150° C.
14. N-(2,3,4-Trimethoxybenzylideneamino)-N'-hydroxyguanidine tosylate, m.p. 179-181° C.
15. N-(2-Hydroxy-4,6-dimethoxybenzylideneamino)-N'-hydroxyguanidine tosylate, m.p. 133-135° C.
16. N-(2,5-Dimethoxybenzylideneamino)-N'-hydroxyguanidine tosylate, m.p. 137-139° C.
17. N-(2,3-Dimethoxybenzylideneamino)-N'-hydroxyguanidine tosylate, m.p. 91-93° C.
18. N-(2,5-Difluorobenzylideneamino)-N'-hydroxyguanidine tosylate, m.p. 186-187.5° C.
19. N-(5-Bromo-2-hydroxybenzylideneamino)-N'-hydroxyguanidine tosylate, m.p. 217-218° C.
20. N-(4-Dimethylaminobenzylideneamino)-N'-hydroxyguanidine tosylate, m.p. 185.5-187° C.
21. N-(4-Nitrobenzylideneamino)-N'-hydroxyguanidine tosylate, m.p. 191-193° C.
22. N-(2-Hydroxy-3-methoxybenzylideneamino)-N'-hydroxyguanidine tosylate, m.p. 173-175° C.
23. N-(3-Chlorobenzylideneamino)-N'-hydroxyguanidine tosylate, m.p. 184-186° C.
24. N-(2-Hydroxybenzylideneamino)-N'-hydroxyguanidine tosylate, m.p. 172-174° C.
25. N-(2,3,4-Tribenzyloxybenzylideneamino)-N'-hydroxyguanidine tosylate, m.p. 147-149° C.
26. N-(Benzylideneamino)guanidine acetate, m.p. 196-198° C.
27. N-(3,4,5-Trimethoxybenzylideneamino)guanidine acetate, m.p. 223-225° C.
28. N-(4-Chlorobenzylideneamino)-N'-hydroxyguanidine tosylate, m.p. 192-194° C.
29. N-(3,4-Methylenedioxybenzylideneamino)-N'-hydroxyguanidine tosylate, m.p. 204-206° C.
30. N-(4-Bromobenzylideneamino)-N'-hydroxyguanidine tosylate, m.p. 199-200° C.
31. N-(4-Diethylaminobenzylideneamino)-N'-hydroxyguanidine tosylate, m.p. 100-102° C.
32. N-(2-Hydroxy-5-nitrobenzylideneamino)-N'-hydroxyguanidine tosylate, m.p. 217-219° C.
33. N-(4-Hydroxybenzylideneamino)-N'-hydroxyguanidine tosylate, m.p. 83-85° C.
34. N-(2,4,6-Trimethoxybenzylideneamino)-N'-hydroxyguanidine tosylate, m.p. 80-82° C.
35. N-(2,3,4-Trihydroxybenzylideneamino)-N'-hydroxyguanidine tosylate, m.p. 100-102° C.
36. N-(3-Hydroxy-4-methoxybenzylideneamino)-N'-hydroxyguanidine tosylate, m.p. 88-89° C.
37. N-(2-Nitrobenzylideneamino)-N'-hydroxyguanidine tosylate, m.p. 204-206° C.
38. N-(2-Bromo-3,4,5-trimethoxybenzylideneamino)-N'-hydroxyguanidine tosylate, m.p. 172-175° C.
39. N-(2,4-Dinitrobenzylideneamino)-N'-hydroxyguanidine tosylate, m.p. 208-211° C.
40. N-(2-Chloro-6-nitrobenzylideneamino)-N'-hydroxyguanidine tosylate, m.p. 92-94° C.
41. N-(3,5-Dimethoxybenzylideneamino)-N'-hydroxyguanidine tosylate, m.p. 92-95° C.
42. N-(5-Hydroxy-2-nitrobenzylideneamino)-N'-hydroxyguanidine tosylate, m.p. 182-183° C.
43. N-(3,6-Dimethoxy-2-nitroxybenzylideneamino)-N'-hydroxyguanidine tosylate, m.p. 101-102° C.
44. N-(3,4-Dimethoxy-2-chlorobenzylideneamino)-N'-hydroxyguanidine tosylate, m.p. 95-97° C.
45. N-(3,4-Dimethoxy-2-chlorobenzylideneamino)guanidine acetate, m.p. 198-200° C.

| | |
|---|---|
| 46 | N-(Benzylideneamino)-N'-hydroxyguanidine tosylate, m.p. 169-171° C. |
| 47 | N-(3,4-Dimethoxy-2-chlorobenzylideneamino)-N'-hydroxy-guanidine 1.5 hydrochloride, m.p. 214-216° C. |
| 48 | N-(2,3-Dimethoxy-5-nitrobenzylideneamino)-N'-hydroxyguanidine tosylate 0.3 hydrate, m.p. 174-176° C. |
| 49 | N-(2,3-Dimethoxy-5-nitrobenzylideneamino)-N'-hydroxyguanidine tosylate 0.3 hydrate, m.p. 174-176° C. |
| 50 | N-(2,3-Dimethoxy-5,6-dinitrobenzylideneamino)-N'-hydroxy-guanidine tosylate 0.15 hydrate, m.p. 178-179° C. |
| 51 | N-(2,6-Dimethoxybenzylideneamino)-N'-hydroxyguanidine tosylate, m.p. 69-71° C. |
| 52 | N-(2,3-Dimethoxy-6-nitrobenzylideneamino)-N'-hydroxyguanidine tosylate, m.p. 81-83° C. |
| 53 | N-(5-Bromo-2,4-dimethoxybenzylideneamino)-N'-hydroxy-guanidine tosylate, m.p. 102-105° C. |
| 54 | N-(2-Fluorobenzylideneamino)-N'-hydroxyguanidine tosylate 0.1 hydrate, m.p. 169-171° C. |
| 55 | N-(2-Methoxybenzylideneamino)-N'-hydroxyguanidine tosylate, m.p. 79-82° C. |
| 56 | N-(2,4,6-Trimethoxybenzylideneamino)guanidine acetate, m.p. 66-68° C. |
| 57 | N-(2,3-Methylenedioxybenzylideneamino)-N'-hydroxyguanidine tosylate, m.p. 163-164.5° C. |
| 58 | N-(4-Bromo-3-nitrobenzylideneamino)-N'-hydroxyguanidine tosylate, m.p. 201-202.5° C. |
| 59 | N-(5-Bromo-2-hydroxy-3-methoxybenzylideneamino)-N'-hydroxy-guanidine tosylate, m.p. 131.5-134° C. |
| 60 | N-(3-Methoxybenzylideneamino)-N'-hydroxyguanidine tosylate, m.p. 151-153.5° C. |
| 61 | N-(2,3-Dinitro-6-chlorobenzylideneamino)-N'-hydroxyguanidine tosylate, m.p. 170-172.5° C. |
| 62 | N-(3,6-Dichloro-2-nitrobenzylideneamino)-N'-hydroxyguanidine tosylate, m.p. 183-184.5° C. |
| 63 | N-(2,6-Dinitrobenzylideneamino)-N'-hydroxyguanidine tosylate, m.p. 91-93° C. |
| 64 | N-(2-Chloro-3,4-dimethoxy-6-nitrobenzylideneamino)-N'-hydroxy-guanidine tosylate, m.p. 104-106.5° C. |
| 65 | N-(2,4-Dinitrobenzylideneamino)guanidine acetate, m.p. 224-226° C. |
| 66 | N-(2-Chlorobenzylideneamino)-N'-hydroxyguanidine tosylate, m.p. 156-158° C. |
| 67 | N-(4-Fluorobenzylideneamino)-N'-hydroxyguanidine tosylate 0.25 hydrate, m.p. 182-184° C. |
| 68 | N-(3-Fluorobenzylideneamino)-N'-hydroxyguanidine tosylate 0.2 hydrate, m.p. 170-171.5° C. |
| 69 | N-(4-Cyanobenzylideneamino)-N'-hydroxyguanidine tosylate 0.2 hydrate, m.p. 203-204° C. |
| 70 | N-(3,5-Dimethoxybenzylideneamino)-N'-hydroxyguanidine tosylate 0.5 hydrate, m.p. 131-133° C. |
| 71 | N-(4-Fluoro-3-nitrobenzylideneamino)-N'-hydroxyguanidine tosylate, m.p. 190-192.5° C. |
| 72 | N-(2-Chloro-5-nitrobenzylideneamino)-N'-hydroxyguanidine tosylate 0.2 hydrate, m.p. 189-191° C. |
| 73 | N-(4-Chloro-2-nitrobenzylideneamino)-N'-hydroxyguanidine tosylate 0.25 hydrate, m.p. 179-181.5° C. |
| 74 | N-(3,4-Dichlorobenzylideneamino)-N'-hydroxyguanidine tosylate, m.p. 200-202.5° C. |
| 75 | N-(2,4-Dichlorobenzylideneamino)-N'-hydroxyguanidine tosylate 0.5 hydrate, m.p. 158-161° C. |
| 76 | N-(4-Methoxy-3-nitrobenzylideneamino)-N'-hydroxyguanidine, m.p. 219-221° C. |
| 77 | N-(2,3-Dichlorobenzylideneamino)-N'-hydroxyguanidine tosylate, m.p. 197-199.5° C. |
| 78 | N-(2-Fluoro-5-nitrobenzylideneamino)-N'-hydroxyguanidine tosylate 0.4 hydrate, m.p. 172-175° C. |
| 79 | N-(2-Methoxy-5-nitrobenzylideneamino)-N'-hydroxyguanidine tosylate 0.7 hydrate, m.p. 115-117° C. |
| 80 | N-(4-Hydroxy-3,5-dimethoxybenzylideneamino)-N'-hydroxy-guanidine tosylate 0.4 hydrate, m.p. 114-115° C. |
| 81 | N-(2-Bromo-5-chloro3-nitrobenzylideneamino)-N'-hydroxy-guanidine tosylate, m.p. 195-196.5° C. |
| 82 | N-(3-Bromo-2,6-dinitrobenzylideneamino)-N'-hydroxyguanidine tosylate 0.5 hydrate 1.8 propanol, m.p. 91-93° C. |
| 83 | N-(3,5-Dinitro-2-methoxybenzylideneamino)-N'-hydroxyguanidine tosylate 0.2 hydrate, m.p. 185-187° C. |
| 84 | N-(5-Bromo-2-hydroxy-3-nitrobenzylideneamino)-N'-hydroxy-guanidine tosylate 0.1 hydrate, m.p. 186-189° C. |
| 85 | N-(3-Nitrobenzylideneamino)guanidine acetate, m.p. 147-148.5° C. |
| 86 | N-(2-Hydroxy-4,6-dimethoxybenzylideneamino)guanidine acetate, m.p. 115-118° C. |
| 87 | N-(4-Nitrobenzylideneamino)guanidine acetate, m.p. 184-186° C. |
| 88 | N-(3-Methoxy-2,6-dinitrobenzylideneamino)-N'-hydroxyguanidine tosylate, m.p. 123.5-125° C. |
| 89 | N-(3-Bromo-4-fluorobenzylideneamino)-N'-hydroxyguanidine tosylate, m.p. 204.5-206.5° C. |
| 90 | N-(2,3-Difluorobenzylideneamino)-N'-hydroxyguanidine tosylate, m.p. 186.5-187° C. |
| 91 | N-(4-Chloro-3-fluorobenzylideneamino)-N'-hydroxyguanidine tosylate 0.5 hydrate, m.p. 166.5-167.5° C. |
| 92 | N-(4-Bromo-3-fluorobenzylideneamino)-N'-hydroxyguanidine tosylate 0.6 hydrate, m.p. 183-185.5° C. |
| 93 | L N-(3-Bromo-4-fluorobenzylideneamino)guanidine acetate, m.p. 172-173.5° C. |
| 94 | N-(2,3-Difluorobenzylideneamino)guanidine acetate, m.p. 149-151.5° C. |
| 95 | N-(4-Chloro-3-fluorobenzylideneamino)guanidine acetate, m.p. 165-171° C. |
| 96 | N-(3-Methoxy-2,6-dinitrobenzylideneamino)guanidine hydrochloride, m.p. 217-218° C. |
| 97 | N-(3-Bromo-2,6-dinitrobenzylideneamino)guanidine hydrochloride, m.p. 166.5-168° C. |
| 98 | N-(2,3-Dimethoxy-5,6-dinitrobenzylideneamino)guanidine acetate, m.p. 165-171° C. |
| 99 | N-(5-Bromo-2,4-dimethoxybenzylideneamino)guanidine acetate 0.5 hydrate, m.p. 221-224° C. |
| 100 | N-(2,3-Dimethoxy-5-nitrobenzylideneamino)guanidine acetate, m.p. 191-194° C. |
| 101 | N-(3,4-Difluorobenzylideneamino)-N'-hydroxyguanidine tosylate, m.p. 199-201° C. |
| 102 | N-(4-Phenylbenzylideneamino)-N'-hydroxyguanidine tosylate, m.p. 171-173° C. |
| 103 | N-(3-Chloro-2,6-dinitrobenzylideneamino)-N'-hydroxyguanidine tosylate, m.p. 85-88° C. |
| 104 | N-(4-Phenylbenzylideneamino)guanadine acetate, m.p. 191-194° C. |
| 105 | N-(3,4-Difluorobenzylideneamino)guanidine acetate, m.p. 176-178° C. |
| 106 | N-(4-Bromo-2-fluorobenzylideneamino)-N'-hydroxyguanidine tosylate 0.3 hydrate, m.p. 176-179° C. |
| 107 | N-(2-Fluoro-5-nitrobenzylideneamino)guanidine acetate, m.p. 192-195° C. |
| 108 | N-(4-Bromo-2-fluorobenzylideneamino)guanidine acetate, m.p. 187-188° C. |
| 109 | N-(2-Bromo-5-nitrobenzylideneamino)-N'-hydroxyguanidine tosylate, m.p. 148-150° C. |
| 110 | N-(2,4-Dinitrobenzylideneamino)-N'-hydroxyguanidine hydrochloride, m.p. 191-193° C. |
| 111 | N-(2,6-Difluorobenzylideneamino)-N'-hydroxyguanidine tosylate, m.p. 176-179° C. |
| 112 | N-(3-Chloro-4-fluorobenzylideneamino)-N'-hydroxyguanidine tosylate, m.p. 198.5-201° C. |
| 113 | N-(3,5-Dichlorobenzylideneamino)-N'-hydroxyguanidine tosylate, m.p. 208-210.5° C. |
| 114 | N-(2-Bromo-4-nitrobenzylideneamino)-N'-hydroxyguanidine tosylate, m.p. 170-173° C. |
| 115 | N-(3,5-Dinitrobenzylideneamino)-N'-hydroxyguanidine tosylate 0.5 hydrate, m.p. 202-207° C. |
| 116 | N-(2,3-Dinitrobenzylideneamino)-N'-hydroxyguanidine tosylate, m.p. 214-216° C. |
| 117 | N-(3,5-Dichlorobenzylideneamino)guanidine acetate, m.p. 131-134° C. |
| 118 | N-(3,5-Dinitrobenzylideneamino)guanidine acetate dihydrate, m.p. 251-254° C. (decomp.) |
| 119 | N-(2,6-Difluorobenzylideneamino)guanidine acetate, m.p. 138.5-141° C. |
| 120 | N-(3-Chloro-4-fluorobenzylideneamino)guanidine acetate, m.p. 141-144° C. |
| 121 | N-(2-Bromo-4-nitroobenzylideneamino)guanidine acetate, m.p. 145-147° C. |
| 122 | N-(2-Bromo-5-nitroobenzylideneamino)guanidine acetate, m.p. 205-208° C. (decomp) |
| 123 | N-(2-Iodobenzylideneamino)-N'-hydroxyguanidine tosylate, m.p. 136-139° C. |
| 124 | N-(2-Iodobenzylideneamino)guanidine acetate, m.p. 1714-173° C. |
| 125 | N-(2,3-Dimethoxy-5-nitrobenzylideneamino)guanidine hydrochloride, m.p. 237-238° C. |

-continued

126 N-(2-Hydroxy-4-methoxybenzylideneamino)-N'-hydroxyguanidine tosylate, m.p. 174-176° C.
127 N-(2-Hydroxy-4-methoxybenzylideneamino)guanidine acetate, m.p. 161-164° C.
128 N-(4-Bromo-3-nitrobenzylideneamino)guanidine acetate, m.p. 152-153° C.
129 N-(6-Chloro-2,3-dinitrobenzylideneamino)guanidine hydrochloride, m.p. 153-154.5° C.
130 N-(3-Bromo-4-methoxybenzylideneamino)guanidine hydrochloride, m.p. 261-262.5° C.
131 N-(3-Iodobenzylideneamino)guanidine hydrochloride, m.p. 203-204° C.
132 N-(3-Iodobenzylideneamino)-N'-hydroxyguanidine tosylate, m.p. 193.5-195° C.
133 N-(2-Sulphobenzylideneamino)guanidine hydrochloride, m.p. >260° C.
134 N-(2-Sulphobenzylideneamino)-N'-hydroxyguanidine, m.p. 243.5-244° C.
135 N-(3,4-Dichlorobenzylideneamino)guanidine acetate, m.p. 138-140° C.
136 N-(2-Chloro-5-nitrobenzylideneamino)guanidine acetate, m.p. 222-224° C. (decomp)
137 N-(4-Chloro-3-nitrobenzylideneamino)guanidine acetate, m.p. 136-139° C. (decomp.)
138 N-(4-Fluoro-3-nitrobenzylideneamino)guanidine acetate, m.p. 222-224° C. (decomp.)
139 N-(4-Methoxy-3-nitrobenzylideneamino)guanidine acetate, m.p. 144-147° C.
140 N-(2-Chloro-3,4,5-trimethoxybenzylideneamino)-N'-hydroxyguanidine tosylate, m.p. 176-178° C.
141 N-(3,5-Difluorobenzylideneamino)-N'-hydroxyguanidine tosylate, m.p. 210.5-213° C.
142 N-(5-Bromo-2,3,4-trimethoxybenzylideneamino)-N'-hydroxyguanidine tosylate, m.p. 195-197° C.
143 N-(3-Chloro-4-methoxybenzylideneamino)-N'-hydroxyguanidine tosylate, m.p. 204-207° C.
144 N-(2,3-Dimethoxy-5-nitrobenzylideneamino)-N'-hydroxyguanidine hydrochloride, m.p. 196-197.5° C.
145 N-(3,5-Difluoro-2-nitrobenzylideneamino)-N'-hydroxyguanidine tosylate, m.p. 176-178° C.
146 N-(3,5-Dichloro-2-nitrobenzylideneamino)-N'-hydroxyguanidine tosylate, m.p. 205-207° C.
147 N-(3,5-Difluoro-2-nitrobenzylideneamino)guanidine acetate, m.p. 231-233° C.
148 N-(3,5-Dichloro-2-nitrobenzylideneamino)guanidine acetate, m.p. 88-91° C.
149 N-(2-Hydroxy-3-methoxy-5-nitrobenzylideneamino)guanidine hydrochloride, m.p. 243-246° C.
150 N-(2-Hydroxy-4-methoxy-5-nitrobenzylideneamino)guanidine hemiacetate, m.p. 227-230° C.
151 N-(3-Chloro-4-methoxy-5-nitrobenzylideneamino)guanidine acetate, m.p. 255-258° C. (decomp.)
152 N-(3,5-Dichloro-4-methoxybenzylideneamino)guanidine acetate, m.p. 185-190° C.
153 N-(3-Bromo-4-methoxy-5-methylbenzylideneamino)guanidine acetate, m.p. 163-166° C.
154 N-(2,3,4-Trimethoxybenzylideneamino)guanidine hydrochloride, m.p. 181-183° C.
155 N-(4-Chloro-2-methoxy-5-nitrobenzylideneamino)guanidine acetate, m.p. 196-199° C.
156 N-(3,6-Dichloro-2-nitrobenzylideneamino)guanidine acetate, m.p. 219.5-221° C.
157 N-(2-Hydroxy-4-methyl-5-nitrobenzylideneamino)guanidine hydrochloride, m.p. 229-230° C.
158 N-(2-Bromo-5-chloro-3-nitrobenzylideneamino)guanidine acetate, m.p. 136.5-137° C.
159 N-(3-Hydroxy-4-methyl-2-nitrobenzylideneamino)guanidine acetate, m.p. 240-241° C.
160 N-(5-Bromo-4-methyl-2-nitrobenzylideneamino)guanidine hydrochloride, m.p. 246.5-248° C.
161 N-(5-Bromo-2-hydroxy-3-nitrobenzylideneamino)guanidine hydrochloride, m.p. >250° C.
162 N-(5-Bromo-2-methoxy-3-nitrobenzylideneamino)guanidine hydrochloride, m.p. 258-259° C.
163 N-(2,4-Dimethoxy-5-nitrobenzylideneamino)guanidine acetate, m.p. 207-210° C.
164 N-(4-Bromo-2-fluoro-5-nitrobenzylideneamino)guanidine acetate, m.p. 175-198° C. (decomp.)

Example 2

This example illustrates the potency of compounds of formula (I) and their therapeutically active acid addition salts for treatment of mental disorders.

Test 1. Affinity for the MC1-receptor

The binding assay was carried out essentially as described by Lunec et al, Melanoma Res 1992; 2; 5-12, using $I^{125}$-NDP-αMSH as ligand.

Test 2. Affinity for the MC3-Receptors, the MC4-Receptors and the MC5-Receptors

The binding assays were carried out essentially as described by Szardenings et al, J Biol Chem 1997; 272; 27943-27948 and Schiöth et al, FEES Lett 1997; 410; 223-228 using $I^{125}$-NDP-αMSH as ligand.

Test 3. cAMP

The stimulation of cAMP was carried out essentially as described by Schiöth et al, Br J Pharmacol 1998; 124; 75-82.

TABLE 1

Affinity for MC-receptors

| | Ki(μM) | | | |
|---|---|---|---|---|
| Compound | MC1 | MC3 | MC4 | MC5 |
| 1:3 | 42 | 91 | 62 | 47 |
| 1:4 | 42 | 68 | 61 | 33 |

TABLE 1b

Influence on cAMP

| | MC1c | MC3c | MC4c | MC5c |
|---|---|---|---|---|
| 1:3 | 8.4 | 16 | 31.8 | 4.7 |
| 1:4 | 6.4 | 1 | 17.1 | 8.7 |

Example 3

The following formulations are representative for all of the pharmacologically active compounds of the invention.

Example of a Preparation Comprising a Capsule

| | Per capsule |
|---|---|
| Active ingredient, as salt | 5 mg |
| Lactose | 250 mg |
| Starch | 120 mg |
| Magnesium stearate | 5 mg |
| Total | up to 385 mg |

In case higher amounts of active ingredient, the amount of lactose used may be reduced.

Example of a Suitable Tablet Formulation.

| | Per tablet |
|---|---|
| Active ingredient, as salt | 5 mg |
| Potato starch | 90 mg |
| Colloidal Silica | 10 mg |
| Talc | 20 mg |

|  | Per tablet |
|---|---|
| Magnesium stearate | 2 mg |
| 5% aqueous solution of gelatine | 25 mg |
| Total | up to 385 mg |

A solution for parenteral administration by injection can be prepared in an aqueous solution of a water-soluble pharmaceutically acceptable acid addition salt of the active substance preferably in a concentration of 0.1% to about 5% by weight. These solutions may also contain stabilising agents and/or buffering agents.

The invention claimed is:

1. A method of treating arthritis, comprising administering an effective amount of N-(2-chloro-3,4-dimethoxybenzylideneamino)guanidine, or a pharmaceutically acceptable salt thereof, to a patient in need thereof.

2. The method as claimed in claim 1, wherein the pharmaceutically acceptable salt is N-(2-chloro-3,4-dimethoxybenzylideneamino)guanidine acetate.

3. The method as claimed in claim 2, wherein the N-(2-chloro-3,4-dimethoxybenzylideneamino)guanidine acetate is present in a pharmaceutical composition together with one or more adjuvants, carriers or excipients.

4. The method as claimed in claim 3, wherein the arthritis is psoriatic arthritis.

5. The method as claimed in claim 2, wherein the arthritis is psoriatic arthritis.

6. The method as claimed in claim 1, wherein the N-(2-chloro-3,4-dimethoxybenzylideneamino)guanidine or a pharmacologically acceptable salt thereof is present in a pharmaceutical composition together with one or more adjuvants, carriers or excipients.

7. The method as claimed in claim 6, wherein the arthritis is psoriatic arthritis.

8. The method as claimed in claim 1, wherein the arthritis is psoriatic arthritis.

* * * * *

UNITED STATES PATENT AND TRADEMARK OFFICE
CERTIFICATE OF CORRECTION

PATENT NO. : 8,410,174 B2  
APPLICATION NO. : 13/426096  
DATED : April 2, 2013  
INVENTOR(S) : Lundstedt et al.

Page 1 of 1

It is certified that error appears in the above-identified patent and that said Letters Patent is hereby corrected as shown below:

On The Title Page

"(75) Inventors: Torbjörn Lundstedt, Uppsala (SE);
  Anna Skottner, Ekerö (SE);
  Elisabeth Seifert, Uppsala (SE)"

should read:

--(75) Inventors: Torbjörn Lundstedt, Uppsala (SE);
  Anna Skottner, Ekerö (SE)--

Signed and Sealed this  
Second Day of August, 2016

Michelle K. Lee  
*Director of the United States Patent and Trademark Office*